United States Patent
Hartley et al.

(10) Patent No.: US 7,488,344 B2
(45) Date of Patent: Feb. 10, 2009

(54) DEVICE AND METHOD FOR TREATING THORACIC AORTA

(75) Inventors: David Ernest Hartley, Subiaco (AU); Ian Nixon, Victoria (AU); Peter John Mossop, Victoria (AU)

(73) Assignees: William A. Cook Australia Pty. Ltd., Queensland (AU); Cook Incorporated, Bloomington, IN (US)

( * ) Notice: Subject to any disclaimer, the term of this patent is extended or adjusted under 35 U.S.C. 154(b) by 797 days.

(21) Appl. No.: 10/726,962

(22) Filed: Dec. 3, 2003

(65) Prior Publication Data
US 2004/0193244 A1    Sep. 30, 2004

Related U.S. Application Data

(60) Provisional application No. 60/430,821, filed on Dec. 4, 2002.

(51) Int. Cl.
*A61F 2/06* (2006.01)
(52) U.S. Cl. .............. 623/1.23; 623/1.11; 623/1.13; 623/1.35; 606/108; 606/150
(58) Field of Classification Search ............. 623/1.11, 623/1.13, 1.23, 1.35, 1.36; 606/108, 150
See application file for complete search history.

(56) References Cited

U.S. PATENT DOCUMENTS

| | | | |
|---|---|---|---|
| 6,773,457 B2 * | 8/2004 | Ivancev et al. | 623/1.28 |
| 6,939,370 B2 * | 9/2005 | Hartley et al. | 623/1.11 |
| 7,074,235 B1 * | 7/2006 | Roy | 623/1.11 |
| 7,147,656 B2 * | 12/2006 | Andreas et al. | 623/1.11 |
| 7,175,652 B2 * | 2/2007 | Cook et al. | 623/1.13 |
| 2002/0151953 A1 * | 10/2002 | Chobotov et al. | 623/1.11 |

* cited by examiner

*Primary Examiner*—Kevin T Truong
*Assistant Examiner*—Katherine M Dowe
(74) *Attorney, Agent, or Firm*—Richard J. Godlewski

(57) ABSTRACT

A prosthesis, introducer device and a method for repair of an aortic aneurysm which is positioned at least partially in the ascending aorta (62). The prosthesis (3) has a proximal end (15) and a distal end (5) and is formed from a biocompatible material, the proximal end is adapted to be surgically fastened adjacent and around the aortic heart valve (60) of a patient and the distal end is adapted to extend into the descending aorta (66). The distal end has a distally extending exposed self-expanding stent (9). The introducer device can be deployed through an incision (75) in the thoracic arch (64) and extend down the descending aorta to place the distal end of the prosthesis first and then removed so that the proximal end of the prosthesis can be sutured in place around the aortic heart valve (60).

7 Claims, 11 Drawing Sheets

DEVICE AND METHOD FOR TREATING THORACIC AORTA

CROSS-REFERENCE TO RELATED APPLICATIONS

This application claims priority of provisional application Serial No. 60/430,821, filed Dec. 4, 2002.

TECHNICAL FIELD

This invention relates to a device and method for treating the thoracic aorta of a patient.

BACKGROUND OF THE INVENTION

Endovascular methods have been proposed for treatment of aneurysm of the aorta particularly where the aneurysm is adjacent the aorta bifurcation but when an aneurysm occurs higher up in the aorta, in the region of the descending aorta adjacent the thoracic arch or in the ascending aorta, endovascular techniques for treating these aneurysms are somewhat more difficult because of the arched nature of the thoracic arch, the occurrence of major arteries in the region and the proximity to the heart.

Generally operations to treat aneurisms of the aorta in this region have been done by open chest surgery by surgical replacement of the aorta with a tubular prosthesis. It is proposed in this invention to use a combination of open chest surgery and endovascular deployment to deploy a prosthesis to treat aneurysms and the like in the thoracic arch area of the aorta.

For this purpose a particular construction of prosthesis is proposed as well as a deployment device and a method and deploying the device into the aorta.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart.

SUMMARY OF THE INVENTION

In one form the invention is said to reside in a prosthesis for repair of an aortic aneurysm which is at least partially in the ascending aorta, the prosthesis being tubular and having a proximal end and a distal end and being formed from a biocompatible material, the proximal end being adapted to be surgically fastened adjacent and around the aortic heart valve of a patient and the distal end being adapted to extend into the descending aorta, the distal end including at least one self-expanding stent.

Preferably the distal end of the prosthesis has an internal self expanding stent and a further uncovered self expanding stent extending therefrom.

There may be provided barbs on the uncovered self expanding stent.

The tubular prosthesis may be formed from a corrugated biocompatible material and be of varying diameter depending on what portion of the aorta it is intended to be deployed into. The prosthesis may also include side branches or a portion adapted for connecting side branches where other major arteries extend from the aorta particularly in the region of the aortic arch.

In a further form the invention is said to reside in a deployment device for an aortic prosthesis adapted to repair an aneurysm at least partially within the ascending aorta, the prosthesis being as described above, the deployment device including a central catheter extending from a proximal end to a distal end, the proximal end being adapted to remain outside a patient and the distal end being adapted to be inserted into the descending aorta of a patient, a nose cone on the distal end of the central catheter, the nose cone including means to retain the distal end of the prosthesis with the assistance of a trigger wire, and a deployment catheter coaxially around the central catheter and slidable longitudinally with respect to the central catheter and means to lock the movement of the deployment catheter with respect to the central catheter, the deployment catheter extending from adjacent the nose cone to a position which in use is outside the patient.

Preferably the deployment device further includes a manipulator sheath coaxially around the deployment catheter and slidable therealong, the manipulator sheath including a fixing boss at a distal end thereof adapted to retain the proximal end of the prosthesis and a grip at a proximal end thereof which is adapted to remain outside the patient in use, the grip being provided to enable manipulation of the manipulation sheath with respect to the deployment catheter.

The trigger wire arrangement may include a first and second trigger wire system and be adapted to retain the distal end of the prosthesis to the deployment catheter and the external stent within the nose cone of the deployment device.

The first trigger wire system may also be adapted to retain the internal self-expanding stent in a retracted position about the deployment catheter.

The second trigger wire system is adapted to prevent movement of the distal end of the prosthesis with respect to the deployment catheter so that while removing the nose cone from the external stent the prosthesis as a whole does not move distally. There is a problem that the barbs could catch within the nose-cone and the prosthesis be moved with the nose cone if it was not retained.

Preferably the nose cone is in the form of a proximally opening capsule which is adapted to retain the uncovered stent in a contracted condition and thereby also retain the barbs within the capsule before the uncovered stent is released.

Preferably the prosthesis tube is held at the distal end of the deployment device to extend back over the catheter and then is turned back inside itself to be fastened to the fixing boss on the manipulation sheath.

There may be provided on the manipulator sheath and slidable therealong a proximal retainer to retain the proximal folded portion of the prosthesis. The proximal retainer may have a grip to enable manipulation of the proximal retainer. The proximal retainer may be funnel shaped and include an annular groove on its outer surface to receive a suture fastening for holding the proximal end of the graft out the retainer.

The suture may extend inside the retainer so that after suturing the proximal folded portion to the aortic arch as discussed later the suture can be cut within the funnel portion to enable it to be removed.

Preferably the means to lock the deployment catheter with respect to the central catheter is a pin vice.

There may be means on the proximal end of the deployment catheter to retain the external end of each of the trigger wire systems and release the trigger wire as required.

There may be provided a haemostatic seal between the deployment catheter and the manipulation sheath at its proximal end.

In a further form the invention is said to reside in a method of deploying a prosthesis within the thoracic arch area of the aorta to repair an aortic aneurysm at least partially within the ascending aorta, the prosthesis being as discussed above and using a deployment device of the type discussed above, the method including the steps of (1) revealing the aorta and making an incision therein in the region of the aortic arch, (2) inserting the deployment device into the incision and extending the deployment device into the descending aorta to a required distance, (3) surgically joining the prosthesis intermediate its ends circumferentially to the aorta distally adjacent of the incision, (4) releasing the distal end of the prosthesis to enable it to engage with the wall of the descending aorta, (5) withdrawing the deployment device and releasing the proximal end of the prosthesis from the deployment device, (6) feeding the prosthesis into the ascending aorta through the incision and surgically fastening the proximal end of the prosthesis around the aortic heart valve and fastening the prosthesis around the branch arteries.

Preferably the step of releasing the distal end of the prosthesis includes the steps of withdrawing a trigger wire to release the internal self-expanding stent while holding the external self-expanding stent within the nose cone of the deployment device, releasing the locking means and advancing the nose cone distally to release the external stent from the nose cone capsule to enable the external stent to expand so that the barbs engage the walls of the descending aorta and retracting the nose cone to the deployment catheter tip.

The step of advancing the nose cone distally to release the external stent from the nose cone capsule may include the step of retaining the internal self-expanding stent during the advancing.

The step of withdrawing the deployment device may include the step of moving the manipulator sheath proximally with respect to the deployment catheter.

In a further form the invention id said to reside in a prosthesis mounted on a deployment device, the prosthesis being tubular and having a proximal end and a distal end and being formed from a biocompatible material, the proximal end being adapted to be surgically fastened adjacent and around the aortic heart valve of a patient and the distal end being adapted to extend into the descending aorta, the distal end including at least one self-expanding stent, the prosthesis being everted and the proximal and distal ends of the prosthesis being fastened to the distal end of the deployment device with the proximal end within the distal end and a central portion of the prosthesis extending proximally.

BRIEF DESCRIPTION OF THE DRAWING

This then generally describes the invention but to assist with understanding reference will now be made to the accompanying drawings which show a preferred embodiment of the invention including the prosthesis, the deployment device and the method of deploying the prosthesis with the assistance of the accompanying drawings.

In the drawings.

DETAILED DESCRIPTION

Figure 1:
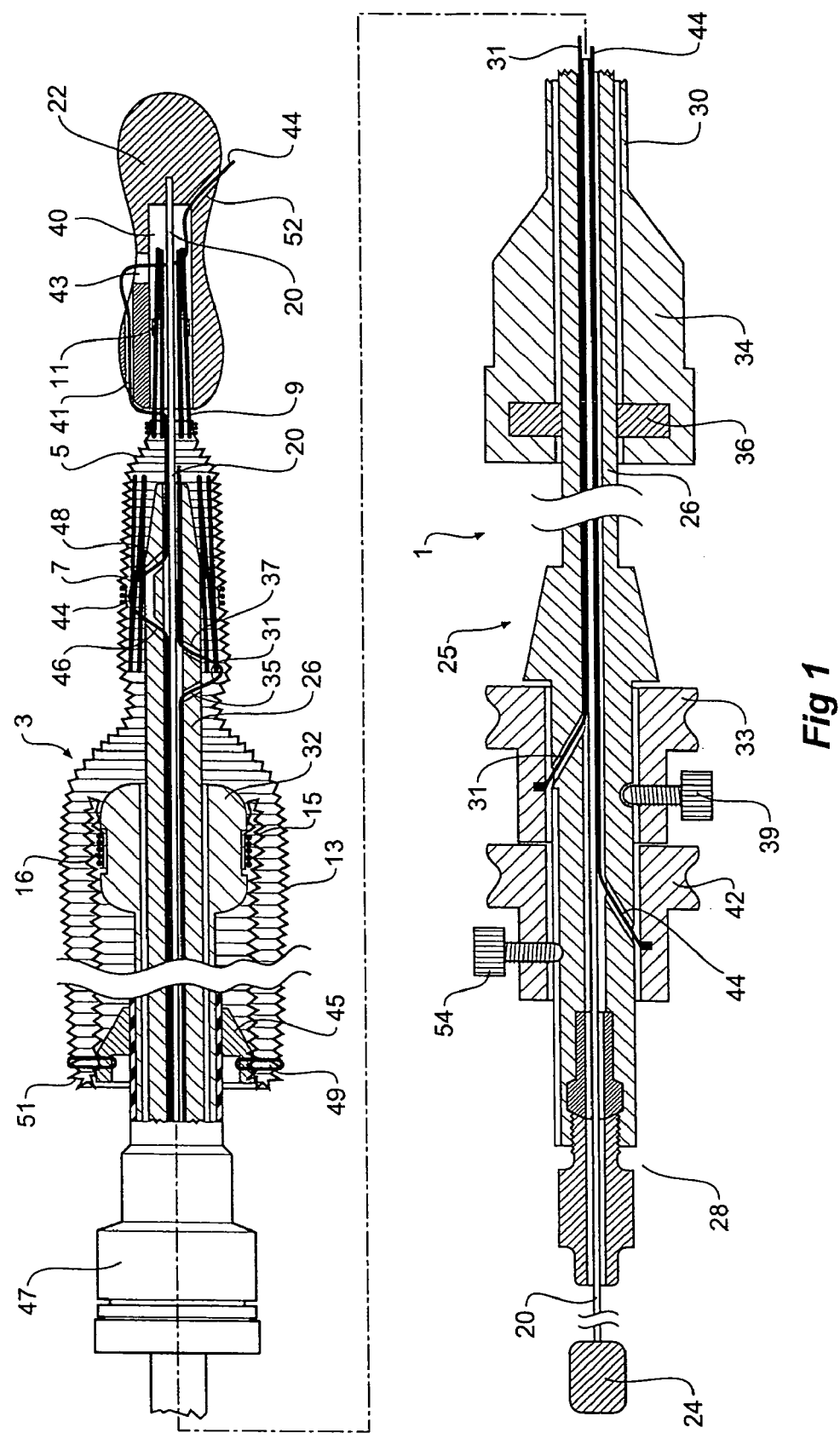
FIG. 1 shows a part cross sectional view of an embodiment of an deployment device according to this invention for deploying a prosthesis into the thoracic aorta.

Now looking more closely at the drawings and in particular FIG. 1 it will be seen that the deployment device 1 has a prosthesis generally shown as 3 mounted onto it. The prosthesis 3 is of generally corrugated form and formed from a biocompatible material. The distal end 5 of the prosthesis has an internal zig-zag stent 7 and a distally extending external stent 9. The external stent 9 has barbs 11 on it but when the prosthesis 3 is loaded onto the deployment device 1 the barbs 11 are contained within nose cone 22 of the deployment device as will be discussed below.

A central portion 13 of the prosthesis 3 extends back over the deployment device and is folded back inside itself until it is mounted at its proximal end 15 to a fixing boss 32 of the deployment device 1 by means of knotted suture 16 as will be discussed later.

The deployment device 1 includes a central guide wire catheter 20 which extends from a nose cone 22 at a distal end of the deployment device to a nose cone actuator 24 at a proximal end of the device. The central catheter 20 is sufficiently flexible to be guided down the descending aorta as will be discussed later. In use, the nose cone actuator 24 is intended to remain outside the patient.

Surrounding the central catheter 20 is a deployment catheter 26. The deployment catheter 26 can be moved longitudinally with respect to the central catheter 20 and can be locked into position with respect to the central catheter by means of pin vice arrangement 28 at the proximal end of a handle 25. The pin vice arrangement 28 and handle 25 is also intended, in use, to remain outside a patient. The handle 25 is at the proximal end of the deployment catheter 26.

Surrounding the deployment catheter 26 is a manipulator sheath 30 which extends from a proximal prosthesis end 15 fixing boss 32 to a proximal end manipulator 34. In use the proximal end manipulator 34 is intended to remain outside a patient. The proximal end manipulator 34 includes a haemostatic seal 36 which engages against the outside of the deployment catheter 26. The haemostatic seal 36 is intended to prevent blood loss between the deployment catheter and the manipulator sheath but also provides frictional engagement and feel between these components.

At the distal end of the deployment device 1 the nose cone 22 includes a recess 40 which provides a capsule into which the external stent 9 of the prosthesis is received and which encloses the barbs 11 on the external stent 9 during deployment.

After release of the pin vice arrangement 28 the nose cone actuator 24 can be moved distally to in turn move the nose cone 22 distally to release the external stent 9 as will be discussed later.

A first trigger wire arrangement is provided to retain the external stent within the nose cone and to hold the internal zig-zag stent in a compressed condition during deployment.

The first trigger wire 44 extends from a trigger wire boss 42 which is mounted onto the handle 25 at the proximal end of the deployment catheter and which in use remains external of the patient to the distal end of the deployment device between the central catheter 20 and the deployment catheter 26 in the lumen of the deployment catheter. Towards the distal end of the deployment device 1 the first trigger wire 44 extends out through a side aperture 46 in the deployment catheter to engage and to retain the internal stent 7 in a retracted condition. This may be done with the assistance of a suture or mooring loop 44 which holds the internal stent in a contracted condition. The suture or mooring loop 44 may remain with the internal stent after deployment or remain with the deployment device.

After the trigger wire 44 engages the internal stent it re-enters a further aperture 48 in the deployment catheter and then extends further distally out of the distal end of the prosthesis 5 and into an aperture 41 in the nose cone 22 to exit the nose cone 22 and re-enter through aperture 43 to engage with the external stent 9 and then exit out a further aperture 52 in the nose cone. The aperture 52 retains the distal end of the trigger wire and prevents it fouling with other objects during deployment.

When the thumb screw 54 in the trigger boss 42 is released the trigger boss 42 can be completely withdrawn which in turns pulls the trigger wire 44 so that it no longer engages the external stent 9 and the internal stent 7. The external stent, however, is still retained within the recess 40 in the nose cone 22 until such time as this is moved distally as will be discussed below and with respect to the drawings showing the various stages of deployment.

A second trigger wire arrangement is provided to retain the internal stent 7 with respect to the deployment catheter during movement of the nose cone 22.

The trigger wire 31 extends from a trigger wire boss 33 which in use remains external of the patient to the distal end of the deployment device between the central catheter 20 and the deployment catheter 26 in the lumen of the deployment catheter. Towards the distal end of the deployment, the catheter trigger wire 31 extends out through a side aperture 35 in the deployment catheter to engage and to retain the internal stent 7.

After the trigger wire 31 engages the internal stent 7 it re-enters a further aperture 37 in the deployment catheter.

When the thumb screw 39 in the trigger boss 33 is released the trigger wire boss 33 can be completely withdrawn which in turns pulls the trigger wire 31 so that it no longer engages the external stent as will be discussed with respect to the drawings showing the various stages of deployment.

A proximal retainer 45 for the prosthesis is mounted coaxially on the manipulator sheath 30 and has a grip 47. The proximal end 51 of the folded prosthesis 13 is retained onto the proximal retainer 45 by means of a loop of suture 49. The proximal retention allows for control of the proximal end of the sheath during deployment as will be discussed later.

Figure 2:
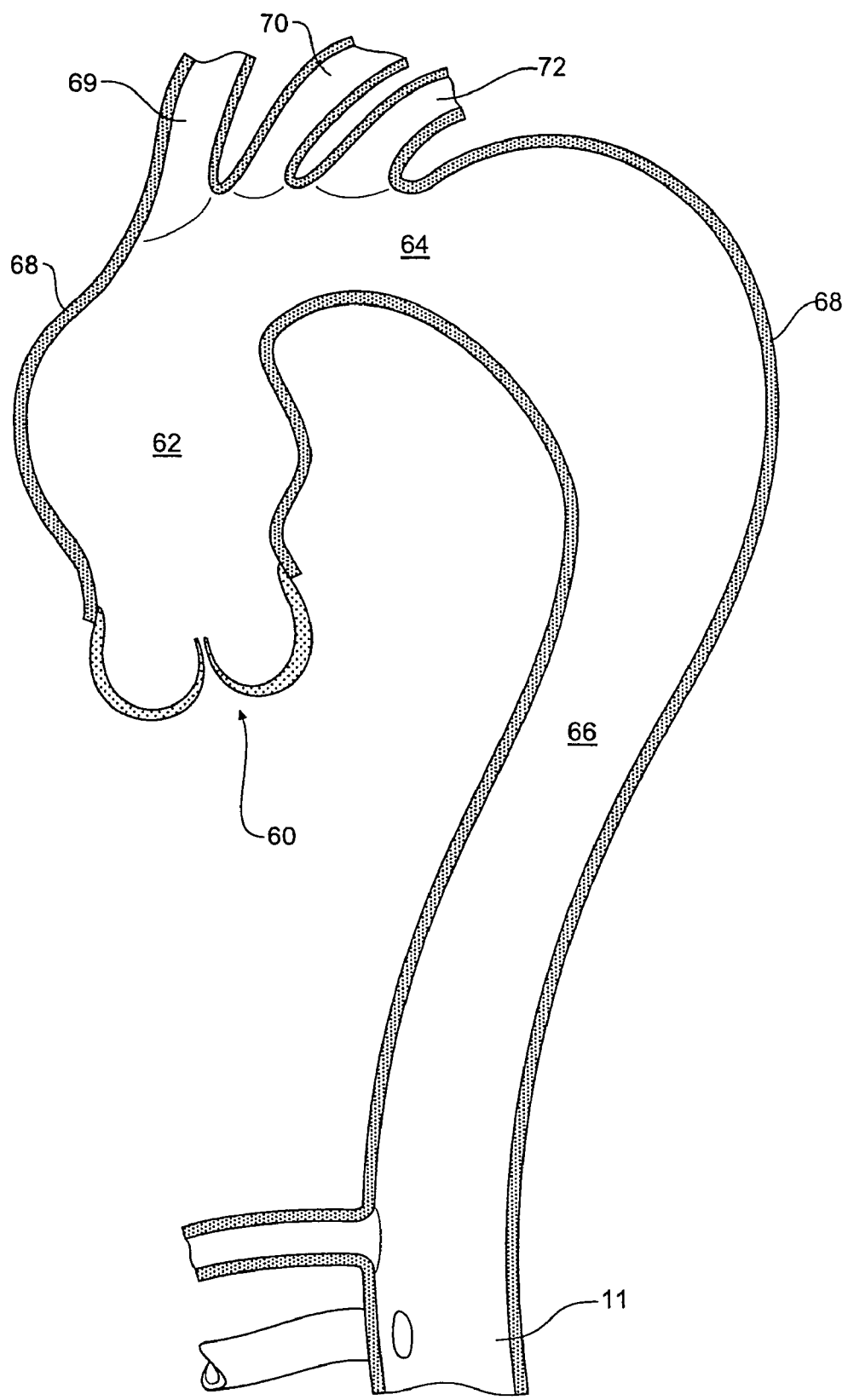
FIG. 2 shows a schematic view of the thoracic aorta showing regions of aneurysm to be treated according to the present invention.

FIG. 2 shows a schematic view of the thoracic arch region of an aorta of a patient. The aorta extends from an aortic valve 60 of a patient via the ascending aorta 62 to the thoracic arch 64 before proceeding down the descending aorta 66. An aneurysm 68 has been depicted in the ascending aorta as well as adjacent the thoracic arch 64 in the descending aorta. In the arch region 64 major arteries, the innominate artery 69, the left common carotid artery 70 and the subclavian artery 72 exit from the aorta. Any deployment of a prosthesis into the aorta must allow blood to still get to these arteries.

Figure 3:
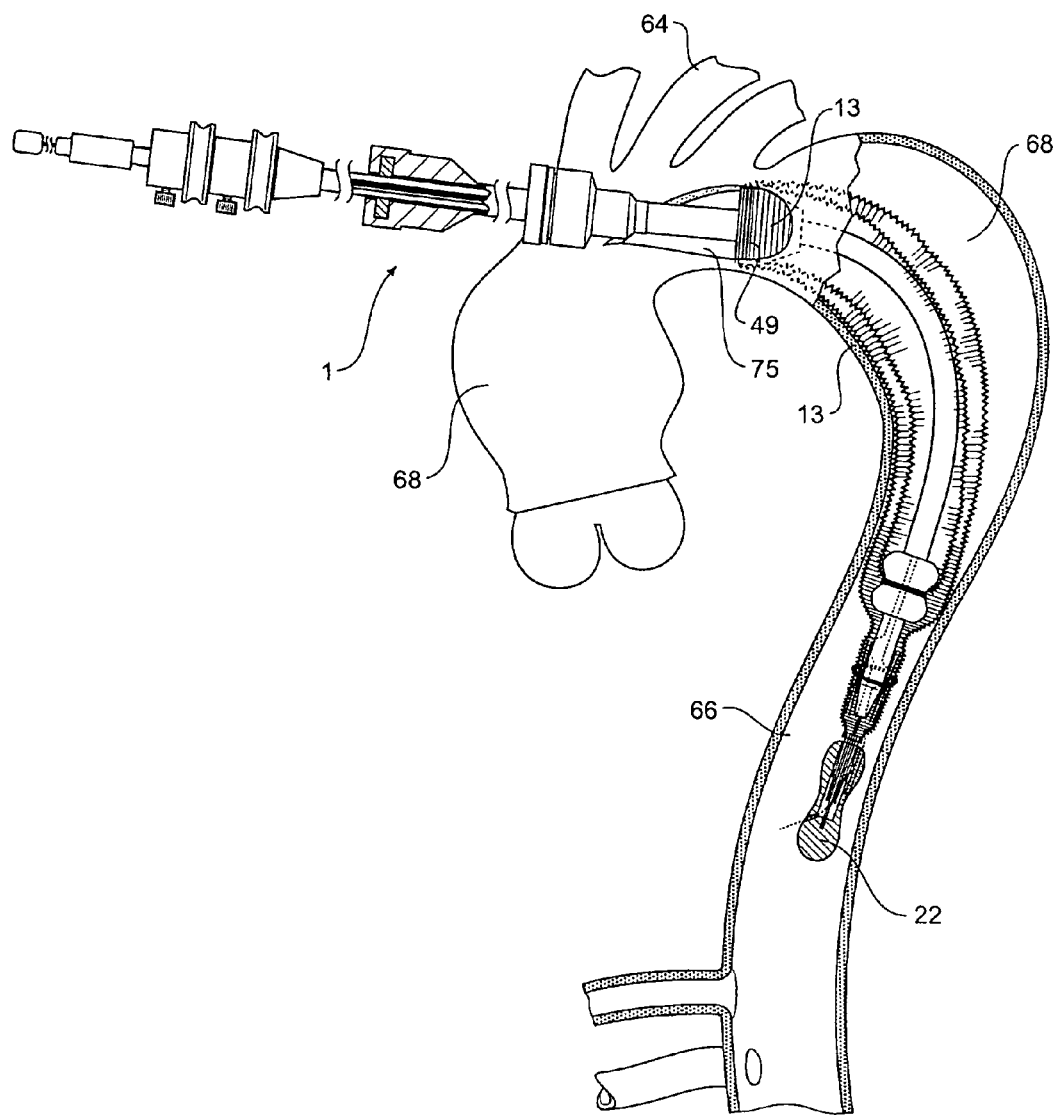
FIG. 3 shows a first stage in the deployment of the prosthesis into the descending aorta.
Figure 4:
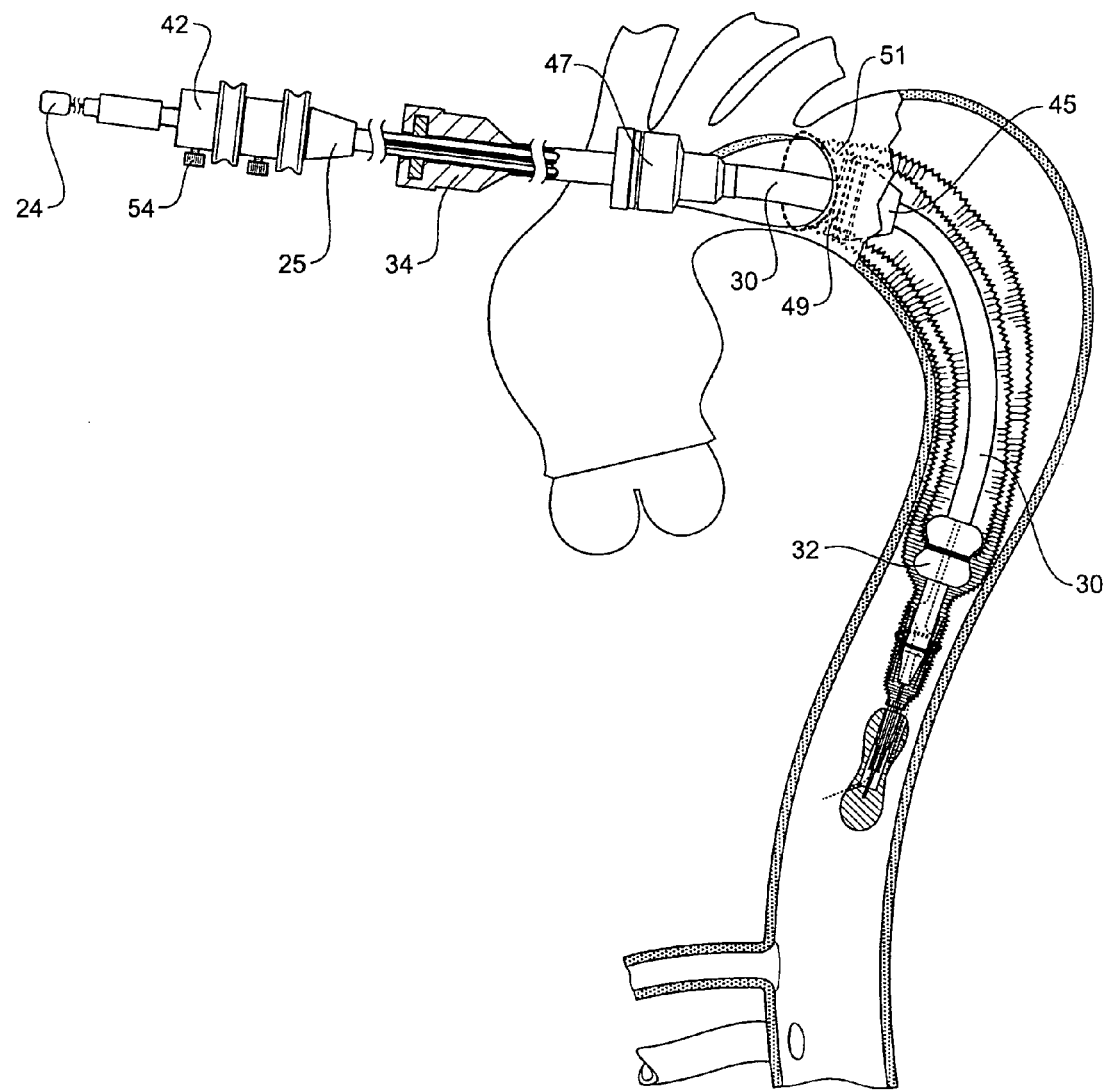
FIG. 4 shows the next stage in the deployment.

As can be seen in FIG. 3 an incision 75 has been made in the side of the thoracic arch 64 of the aorta and the deployment device 1 with the prosthesis mounted onto it has been inserted so that it extends down the descending aorta 66. The deployment device has been deployed to the extent that the nose cone 22 is well past the aneurysm region 68. The central portion of the prosthesis 13 extends back along the deployment device 1 so that it is still visible in the incision 75. The central portion 13 is then fastened circumferentially to the aortic arch as is shown in FIG. 4 just distally of the subclavian artery 72. The prosthesis is sutured or stapled or otherwise fastened completely around its circumference at this point to the wall of the aorta. The proximal retainer 45 assists in holding the proximal end 51 of the folded prosthesis during this fastening.

In the next stage the suture 49 is cut and the grip 47 is moved distally to remove the proximal retainer 45.

Figure 5:
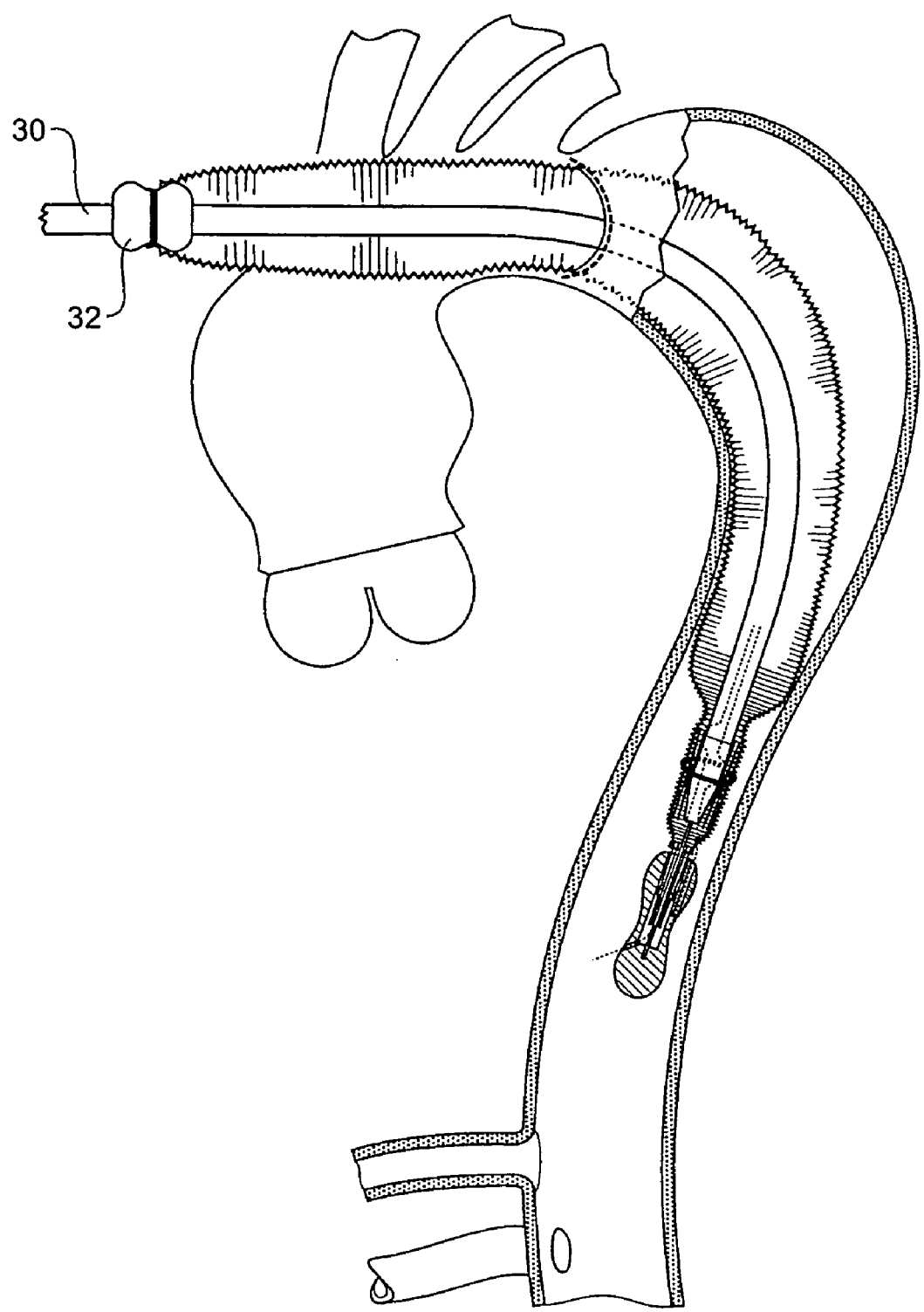
FIG. 5 shows the next stage of deployment where the portion of the prosthesis folded back inside itself is withdrawn.

The prosthesis can then be straightened out by pulling on the proximal end manipulator 34 while holding the handle 25 stationary so that the manipulator sheath 30 withdraws the fixing boss 32 until the position shown in FIG. 5 is attained.

Figure 6:
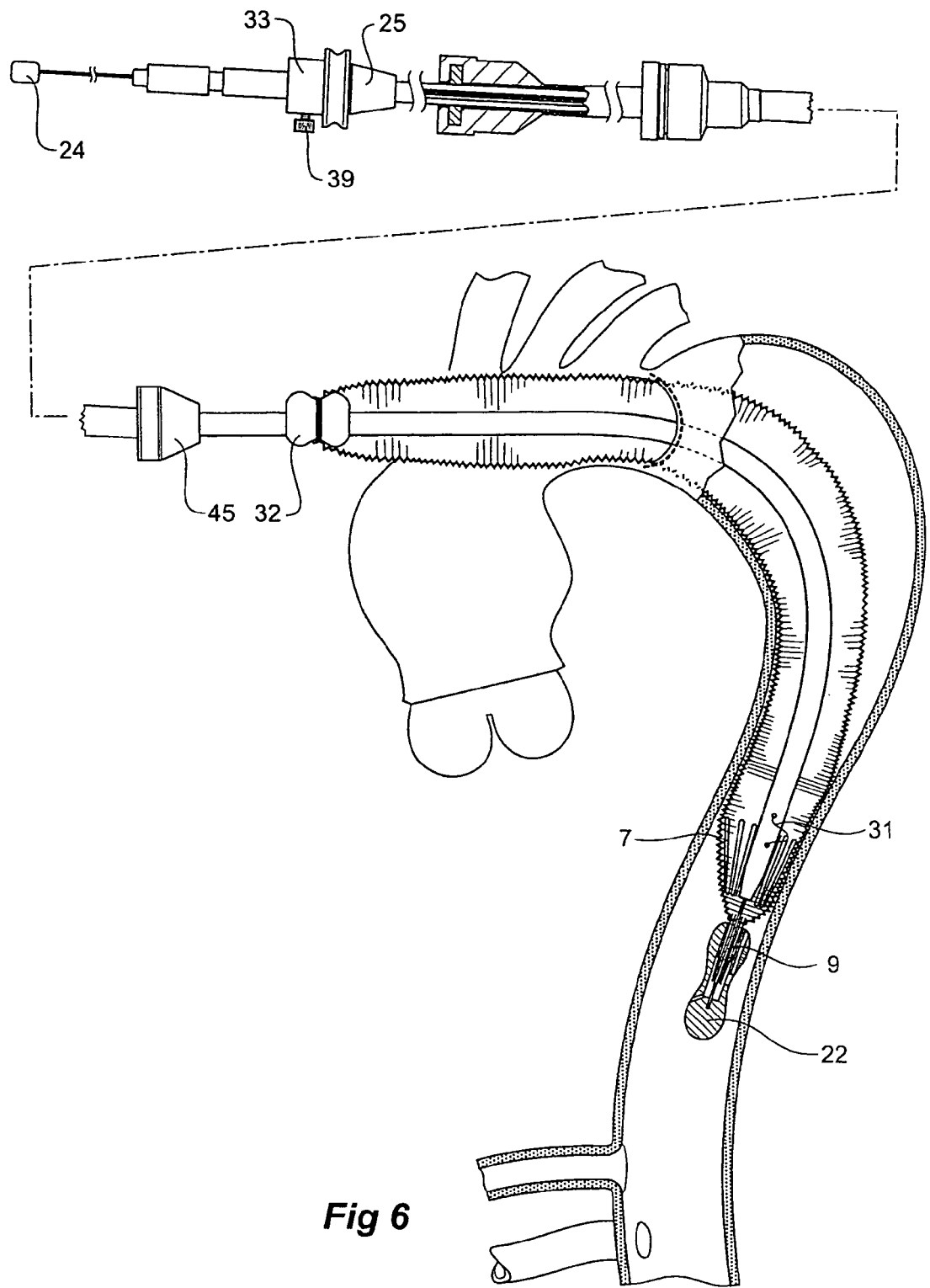
FIG. 6 shows the next stage in which the distal end of the prosthesis is partially released.

In the next stage the first trigger wire boss 42 is completely removed from the handle 25 by releasing the thumb screw 54 and withdrawing the trigger wire boss 42 over the nose cone actuator 24. By this means, trigger wire 44 is removed completely from the nose cone 22 and from retaining the external and internal stents 9, 7. At this stage then as shown in FIG. 6 it will be seen that the internal stent 7 has partially expanded but that the external stent 9 is still retained within the nose cone 22.

Figure 7:
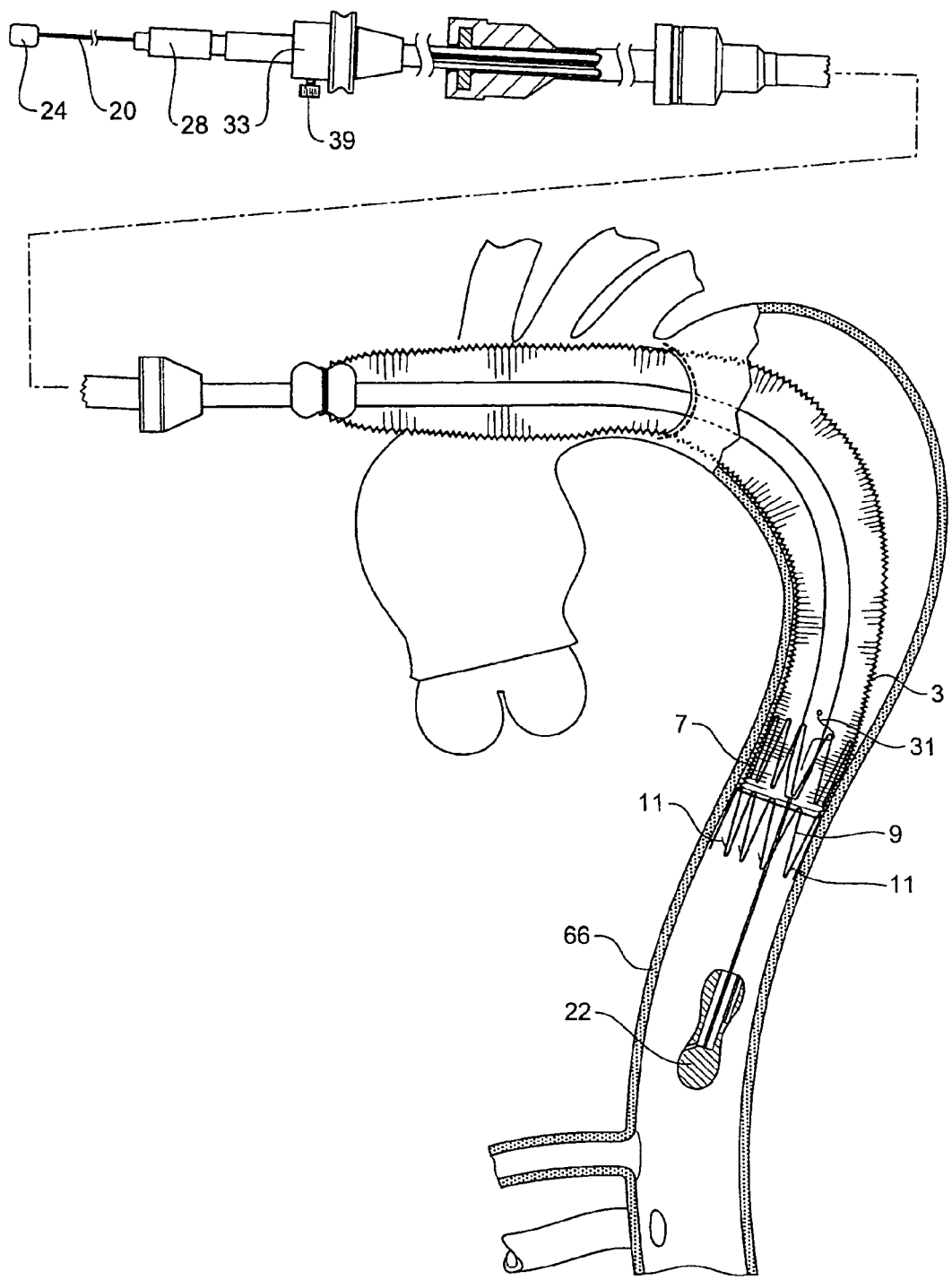
FIG. 7 shows the next stage in the deployment where the distal end of the prosthesis is fully released.

In the next stage as shown in FIG. 7 the pin vice 28 is released and the nose cone activator 24 advanced distally so that by moving the catheter 20 fixed to the activator 24 the nose cone 22 moves distally and releases the external stent 9 from the recess 40 which enables the external stent 9 to expand to the wall of the descending aorta 66 and the barbs 11 to engage into the wall of the aorta to hold the distal ends of the prosthesis 3 in the descending aorta.

At this stage the internal stent 7 is retained by the trigger wire 31. This prevents the prosthesis moving distally while the nose cone is being moved distally.

Figure 8:
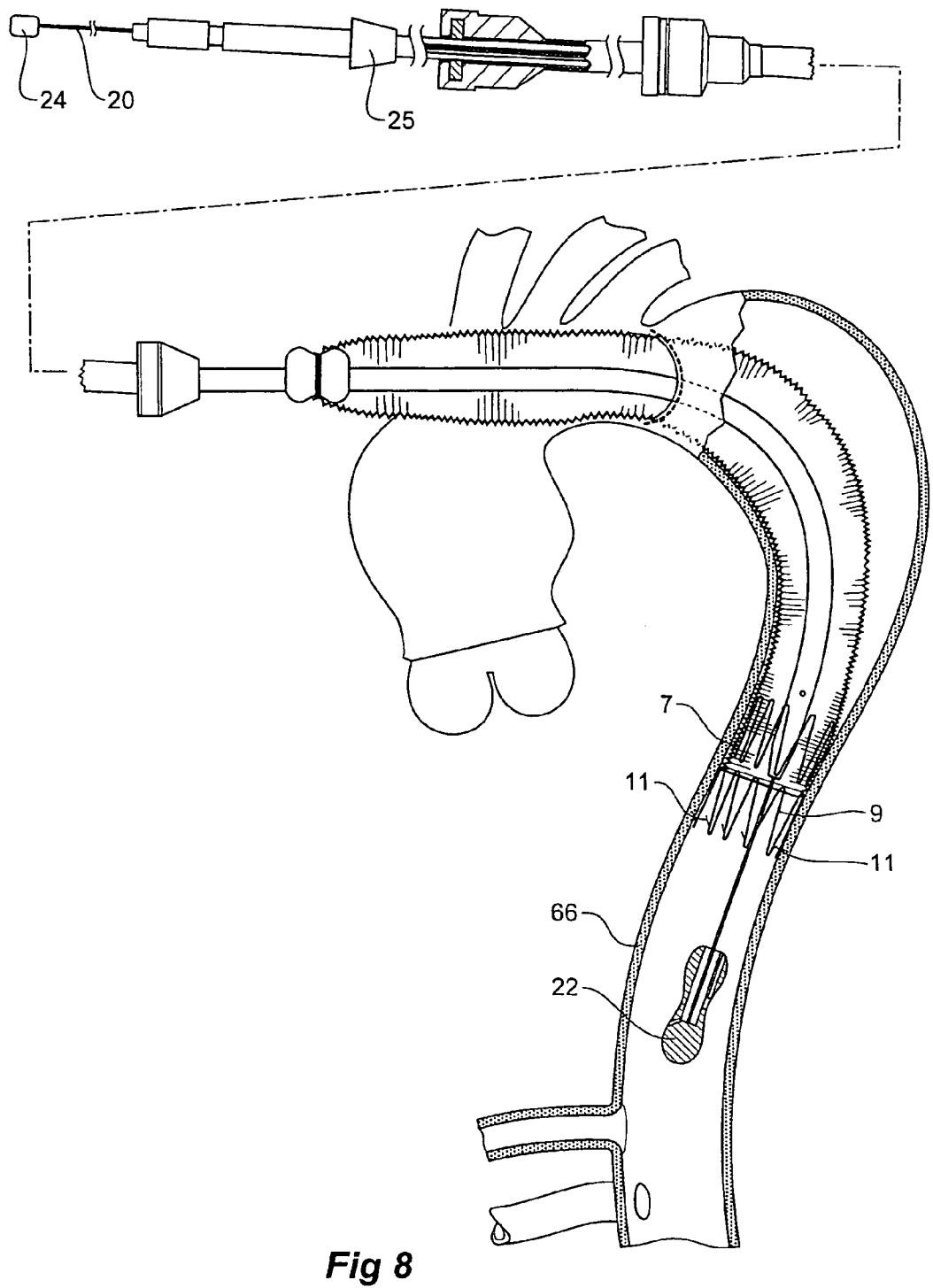
FIG. 8 shows a still further stage with withdrawal of the trigger wire retaining the stented portion of the prosthesis.

Next the second trigger wire boss 33 is completely removed from the handle 25 by releasing the thumb screw 39 and withdrawing the trigger wire boss 33 over the nose cone actuator 24. By this means, trigger wire 31 is removed completely and the internal stent 7 can fully expand to engage the wall of the aorta. This is shown in FIG. 8.

Figure 9:
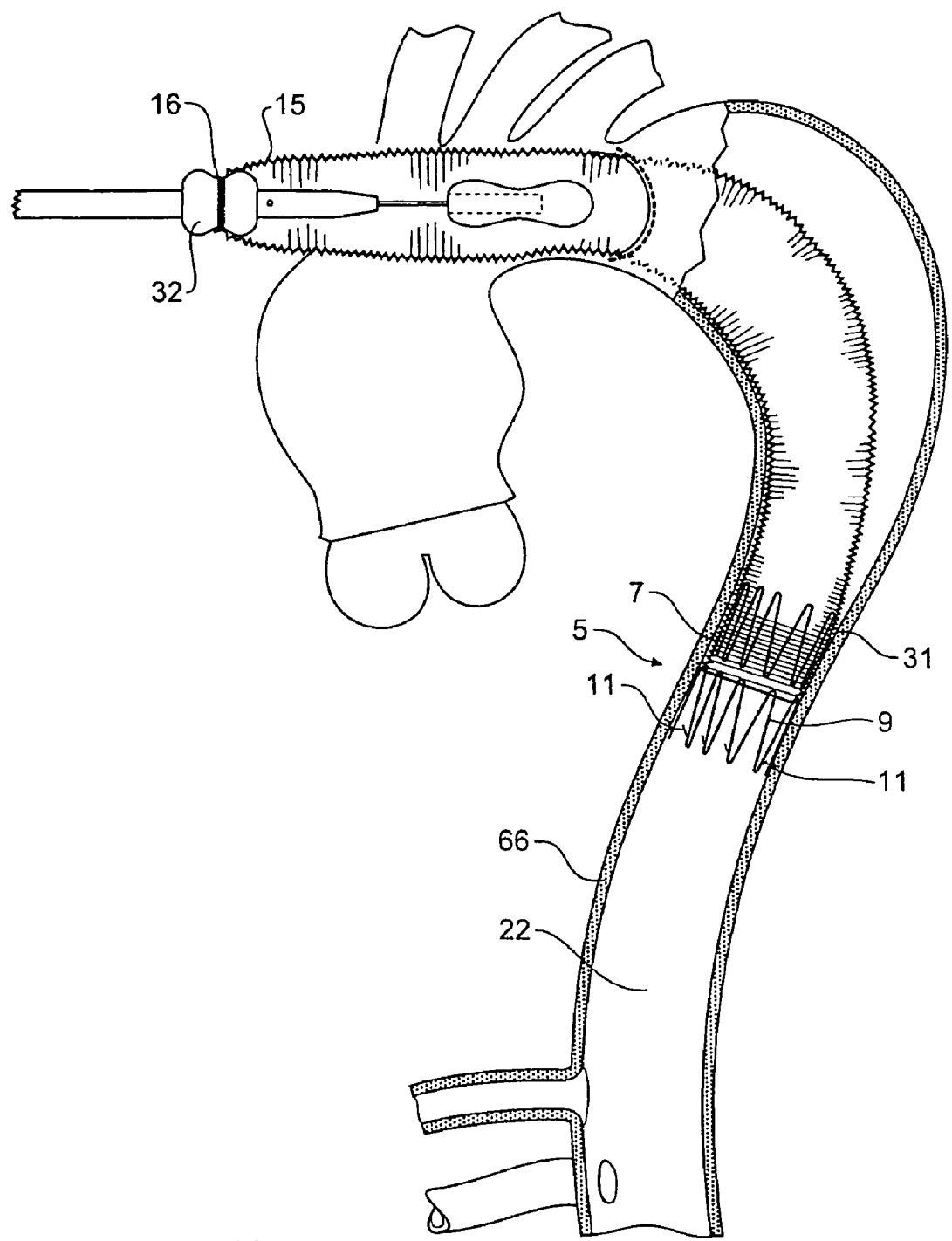
FIG. 9 shows withdrawal of the nose portion of the deployment device.

The nose cone 22 and catheter 20 and deployment device 1 are then retracted towards the fixing boss 32 as shown in FIG. 9 leaving part of the prosthesis deployed in the descending aorta from the central portion 13 sutured into the aortic arch down to the distal end 5 of the prosthesis 3 retained by the internal stent 7 and external stent 9 and barbs 11.

Figure 10:
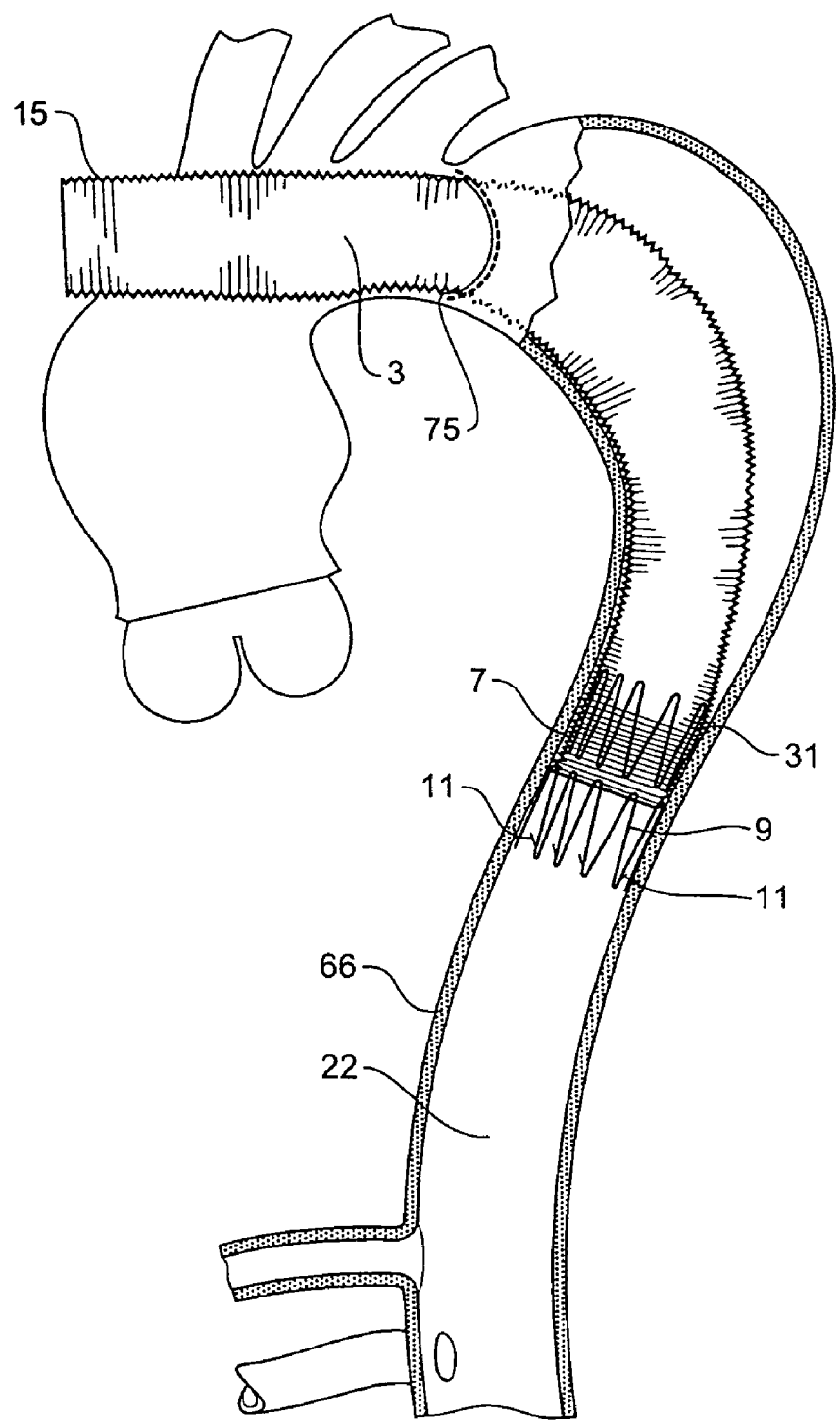
FIG. 10 shows removal of the deployment device.

At this stage of the withdrawal the end 15 of the prosthesis 3 fastened to the graft fixing boss 32 is exposed and the fastening 16 which fastens the graft end 15 to the fixing boss 32 is removed and the deployment device is completely removed from the prosthesis 3 as shown in FIG. 10.

In the next stage of the procedure the proximal end 15 of the prosthesis 3 is fed back into the incision 75 in the aortic arch and directed down the ascending aorta towards the aortic valve 60. The proximal end of the graft 15 is then sutured circumferentially at 80 around the aortic valve 60 so that blood can flow out of the valve and into the prosthesis end 15.

Figure 11:
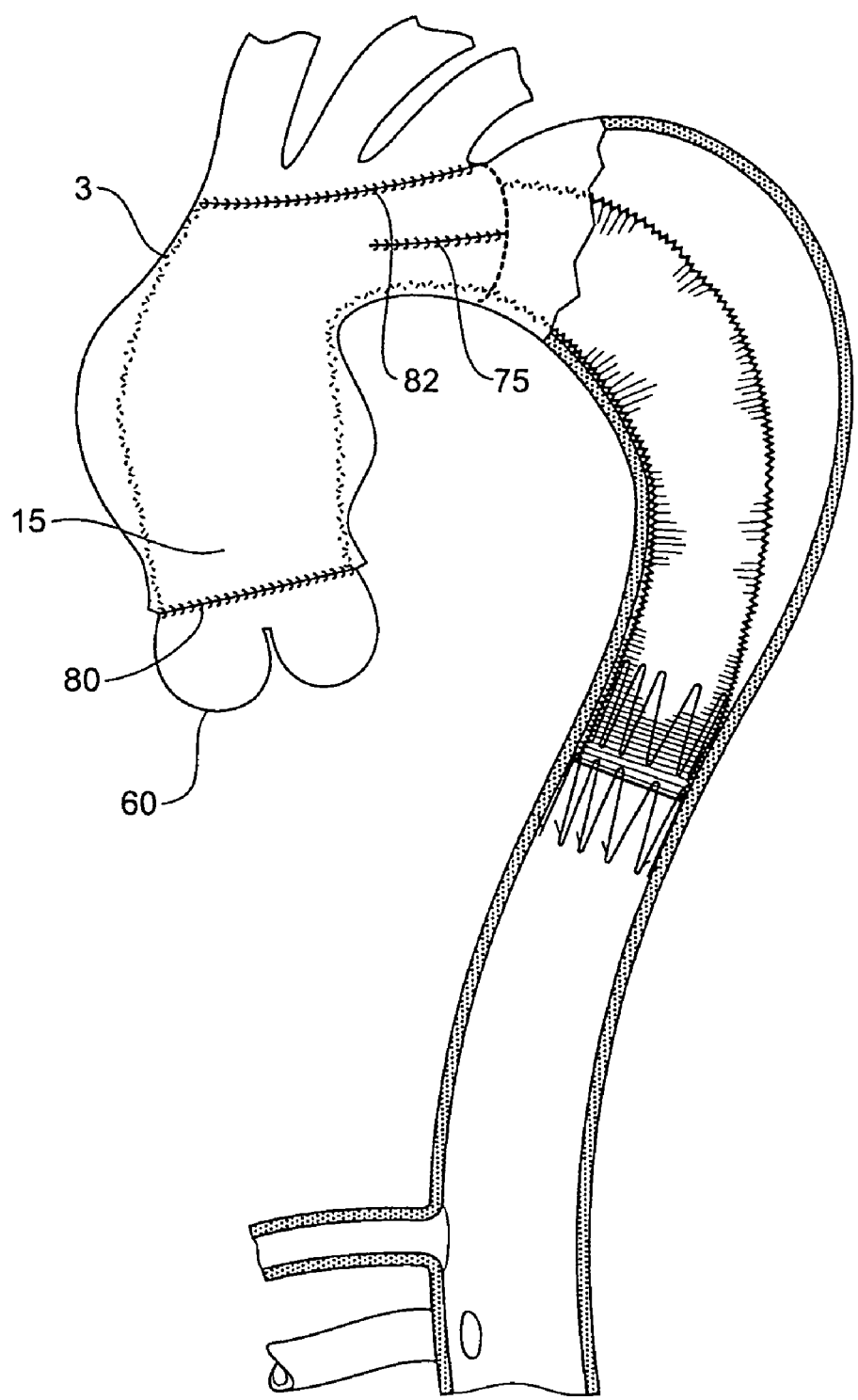
FIG. 11 shows the final suturing in of the prosthesis according to this invention around the aortic valve and the branching arteries.

In the region of the branching arteries an incision 82 is made in the side of the prosthesis 3 and the prosthesis 3 is sutured around the branch arteries so the blood can flow into them as well. The incision 75 is then closed up as shown in FIG. 11 and the chest cavity closed.

Throughout this specification, various indications have been given as to the scope of the invention but the invention is not limited to any one of these but may reside in two or more of these combined together. The examples are given for illustration and not for limitation.

What is claimed is:

1. A deployment device and prosthesis in combination, the prosthesis being mounted on the deployment device, the deployment device comprising a central catheter extending from a proximal end to a distal end, the proximal end in use remaining outside a patient and the distal end in use being inserted into the descending aorta of a patient, a nose cone on the distal end of the central catheter, the nose cone including means to retain the distal end of the prosthesis with the assistance of a trigger wire, and a deployment catheter co-axially around the central catheter and slidable longitudinally with respect to the central catheter and means to lock the movement of the deployment catheter with respect to the central catheter, the deployment catheter extending from a distal end thereof adjacent the nose cone to a position which in use is outside the patient, a manipulator coaxially around the deployment catheter, the manipulator being slidable longitudinally with respect to the deployment catheter and extending to a position which in use is outside the patient the prosthesis being tubular and having a proximal end and a distal end and being formed from a biocompatible material, the proximal end to be surgically fastened adjacent and around the sortic heart valve of a patient and the distal end to extend in use into the descending aorta, the distal end including at least one self-expanding stent, the prosthesis being averted and the proximal and distal ends of the prosthesis extending towards the distal end of the deployment device with the proximal end within the distal end and a central portion of the prosthesis extending proximally and wherein the central portion of the prosthesis is releasably mounted to the manipulator, the proximal end of the prosthesis is fastened to the distal end of the deployment catheter and the distal end of the prosthesis is fastened to the nose cone dilator.

2. A prosthesis mounted on a deployment device as in claim 1 wherein the distal end of the prosthesis has an internal self expanding stent and a further uncovered self expanding stent extending therefrom.

3. A prosthesis mounted on a deployment device as In claim 2 wherein there are barbs on the uncovered self expanding stent.

4. A deployment device as in claim 3 wherein the nose cone is in the form of a proximally opening capsule to retain the uncovered stent in a contracted condition and thereby also retain the barbs within the capsule before the uncovered stent is released from the nose cone.

5. A prosthesis mounted on a deployment device as in claim 1 wherein the tubular prosthesis is formed from a corrugated biocompatible material.

6. A prosthesis mounted on a deployment device as in claim 1 further including a trigger wire arrangement to retain the distal end of the prosthesis within the nose cone of the deployment device.

7. A prosthesis mounted on a deployment device as in claim 1 wherein the trigger wire also retains the internal self-expanding stent in a retracted position about the deployment catheter.

* * * * *